US006570607B1

(12) United States Patent
Fujita

(10) Patent No.: US 6,570,607 B1
(45) Date of Patent: May 27, 2003

(54) LIGHT AND SHADE INSPECTING APPARATUS AND LIGHT AND SHADE INSPECTING METHOD

(75) Inventor: Minoru Fujita, Kawasaki (JP)

(73) Assignee: Toshiba Engineering Corporation, Kawasaki (JP)

( * ) Notice: Subject to any disclaimer, the term of this patent is extended or adjusted under 35 U.S.C. 154(b) by 0 days.

(21) Appl. No.: 09/285,747

(22) Filed: Apr. 5, 1999

(30) Foreign Application Priority Data

Jul. 21, 1998  (JP) ............................................ 10-205252

(51) Int. Cl.7 ................................................. H04N 7/18
(52) U.S. Cl. ..................... 348/125; 382/275; 356/237.2
(58) Field of Search ....................... 356/237.2; 382/275; 250/208.1, 550.45; 348/125

(56) References Cited

U.S. PATENT DOCUMENTS 5,091,963 A    2/1992  Litt et al.
5,774,177 A    6/1998  Lane

FOREIGN PATENT DOCUMENTS

EP     0 311 991 A2    4/1989
EP     0 428 751 A1    5/1991

Primary Examiner—Chris Kelley
Assistant Examiner—George A Bugg, Jr.

(74) Attorney, Agent, or Firm—McGinn & Gibb, PLLC

(57) ABSTRACT

A light-and-shade inspecting apparatus and method therefor, includes an image pick-up device for picking up an image of the object to output an image data, an integrated image calculating portion for dividing the image data outputted from the image pick-up device into a mesh pattern of meshes and then adding together the image data within each of the divided meshes to obtain an integrated image, a differentiated image calculating portion for performing a difference operation between each pair of meshes separated by a predetermined interval from each other with respect to their corresponding two integrated images obtained through the integrated image calculating portion, a defect detecting portion for comparing a value obtained through the differentiated image calculating portion with a predetermined value to detect as a defect portion which is partially different in luminance from the other portions on the object, an average value calculating portion for calculating an average value of the integrated image obtained through the integrated image calculating portion, and a light-and-shade deciding portion for deciding whether the defect detected by the defect detecting portion includes a light defect or a shade defect based on the average value obtained through the average value calculating portion and values of the integrated images in respective pairs of meshes apart by the predetermined interval from each other which have been subjected to the difference operation. Thus, low contrast defects can be precisely detect by distinguishing light and shade defects from each other and without mistaking a single defect for two separate defects.

23 Claims, 3 Drawing Sheets

LIGHT AND SHADE INSPECTING APPARATUS AND LIGHT AND SHADE INSPECTING METHOD

BACKGROUND OF THE INVENTION

1. Field of the Invention

The present invention relates to a light-and-shade inspecting apparatus and method for inspection of a low contrast light-and-shade defect, such as a contaminant, cloudiness etc., on a plain material roll (or web) such as a paper, film and nonwoven fabric, etc., based on an image data which is produced by an image pick-up device picking up the web having a certain width and traveling in one direction.

More particularly, the light-and-shade inspecting apparatus and method also are capable of distinctly judging between a low contrast defect as a shade defect or a light defect.

2. Description of the Related Art

FIG. 4 is a block diagram showing a conventional light and shade inspecting apparatus 11, as disclosed in Japanese (examined) Patent Publication No. 7-99355, for detecting low contrast light and shade.

The light-and-shade inspecting apparatus 11 includes an area sensor portion 13, a brightness information adding portion 15 coupled to an output of the area sensor portion 13, an amount of change calculating portion 17 coupled to an output of the brightness information adding portion 15, a detecting portion 11 coupled to an output of the amount of change calculating portion 17, and a display portion 21 coupled to outputs of the area sensor portion 13, adding portion 15, amount of change calculating portion 17 and detecting portion 19.

The area sensor portion 13 picks up an image of a web as an object to be inspected, and obtains brightness information of each pixel of a plurality of pixels arranged in a two-dimensional. array.

The brightness information adding portion 15 is adapted for sectioning (e.g., dividing) the two-dimensional array of pixel brightness information, which is obtained through the area sensor portion 13, into a plurality of grids of rows and columns of pixels, and then obtaining an added value at each grid by adding together brightness information of the respective pixels within each grid.

The amount of change calculating portion 17 is adapted for obtaining horizontal and vertical changes in an amount of the brightness added value between each pair of grids and within a range of 3 rows and 3 columns of each grid. More particularly, the amount of change calculating portion 17 performs a difference processing or differential processing so as to form a differentiating filter.

The detecting portion 19 is adapted for detecting a mottle (e.g., a low contrast light-and-shade portion such as a mark, streak, blotch, etc.) on the web based on the vertical and horizontal changes in an amount of the brightness.

With the conventional light and shade inspecting apparatus, a low contrast light-and-shade portion such as a contaminant, cloudiness, etc., on the web, can be detected. However, the differential processing is performed in the amount of change calculating portion and then, based on the resultant value sizes, a low contrast light-and-shade defect is detected. Therefore, it is impossible to judge whether the defect thus detected is a light defect or a shade defect.

Moreover, erroneous detection of one defect as two defects may occur since a portion (e.g., an end) of the defect may surge and sag in its differentiated value through the differential processing thereof. Thus, one defect could be erroneously detected as two defects, thereby erroneously raising the total number of defects present on the web.

SUMMARY OF THE INVENTION

In view of the foregoing and other problems of the conventional apparatuses and techniques, an object of the present invention is to overcome the conventional problems and to provide a light-and-shade inspecting apparatus and a light-and-shade inspecting method, which allow low contrast defects to be precisely detected by distinguishing light and shade from each other and without mistaking only one defect for two defects.

To achieve the above and other objects, in a first aspect, a light-and-shade inspecting apparatus according to the present invention for picking up an image of an object to be inspected, and then, based on such image data, inspecting a light and shade on the object, includes:

an image pick-up device for picking up an image of the object to output an image data;

an integrated image calculating portion for dividing the image data outputted from the image pick-up device into a mesh pattern of meshes which are equivalent in area to each other and then adding together the image data within each of the divided meshes to obtain an integrated image;

a differentiated image calculating portion for performing a difference (e.g., differential) operation between each pair of meshes apart by a predetermined interval from each other with respect to their corresponding two integrated images obtained through the integrated image calculating portion;

a defect detecting portion for comparing a value obtained through differentiated image calculating portion with a predetermined value to detect a defect a portion which is partially different in lightness from other portions on the object;

an average value calculating portion for calculating an average value of the integrated image obtained through the integrated image calculating portion; and a light-and-shade judging portion for judging whether the defect detected by the defect detecting portion includes a light defect or a shade defect based on the average value obtained through the average value calculating portion and values of the integrated images in the predetermined pairs of meshes apart a predetermined interval from each other which have been subjected to the difference operation.

Additionally, in the light-and-shade inspecting apparatus according to the present invention, the light-and-shade judging portion functions to subtract the average values of the integrated images in the predetermined pairs of meshes apart from each other from the values of the integrated images to produce the respective subtracted values, and, when one of the subtracted values is larger in absolute value than another of the subtracted values and that the subtracted value in connection with the mesh corresponding to the one of the subtracted values is larger than zero (0), judges the defect in the mesh corresponding to the one of the subtracted values to be a light defect.

Furthermore, in the light-and-shade inspecting apparatus according to the present invention, the light-and-shade judging portion functions to subtract the average values of the integrated images in the predetermined pairs of meshes apart from each other from the respective values of the corresponding integrated images to produce the respective subtracted values, and, when one of the subtracted values is larger in absolute value than another of the subtracted values and that the subtracted value in connection with the mesh corresponding to the one of the subtracted values is negative, judges the defect in the mesh corresponding to the one of the subtracted values to be a shade defect.

In a second aspect of the present invention, a light-and-shade inspecting method, includes:

picking up an image of an object to obtain an image data;

dividing an image composed of the image data into a mesh pattern of meshes which are equivalent in area to each other and then adding together the image data within each of the divided meshes to obtain an integrated image;

performing a difference operation between each pair of meshes separated by a predetermined interval from each other with respect to their corresponding two integrated images to obtain a differentiated image;

comparing a value obtained from the differentiated image with a predetermined value to detect as a defect a portion which is at least partially different in lightness from the other on the object;

calculating an average value of the integrated image; and judging whether the defect includes a light defect or a shade defect based on the average value and values of the respective integrated images in each pair of meshes apart a predetermined interval from each other which have been subjected to the difference operation.

Thus, unlike the conventional apparatus, the present invention precisely detects low contrast defects by distinguishing light-and-shade from each other and without mistaking a single defect for two defects.

The present disclosure relates to subject matter contained in Japanese Patent Application No. 10-205252, filed Jul. 21, 1998, which is expressly incorporated herein by reference in its entirety.

BRIEF DESCRIPTION OF THE DRAWINGS

The above and other objects, features and advantages of the present invention will become apparent from the following detailed description of the invention taken in conjunction with the accompanying drawings in which.

DETAILED DESCRIPTION OF A PREFERRED EMBODIMENT OF THE PRESENT INVENTION

Hereinafter, a preferred embodiment of the present invention will be described in detail with reference to the accompanying drawings.

Figure 1:
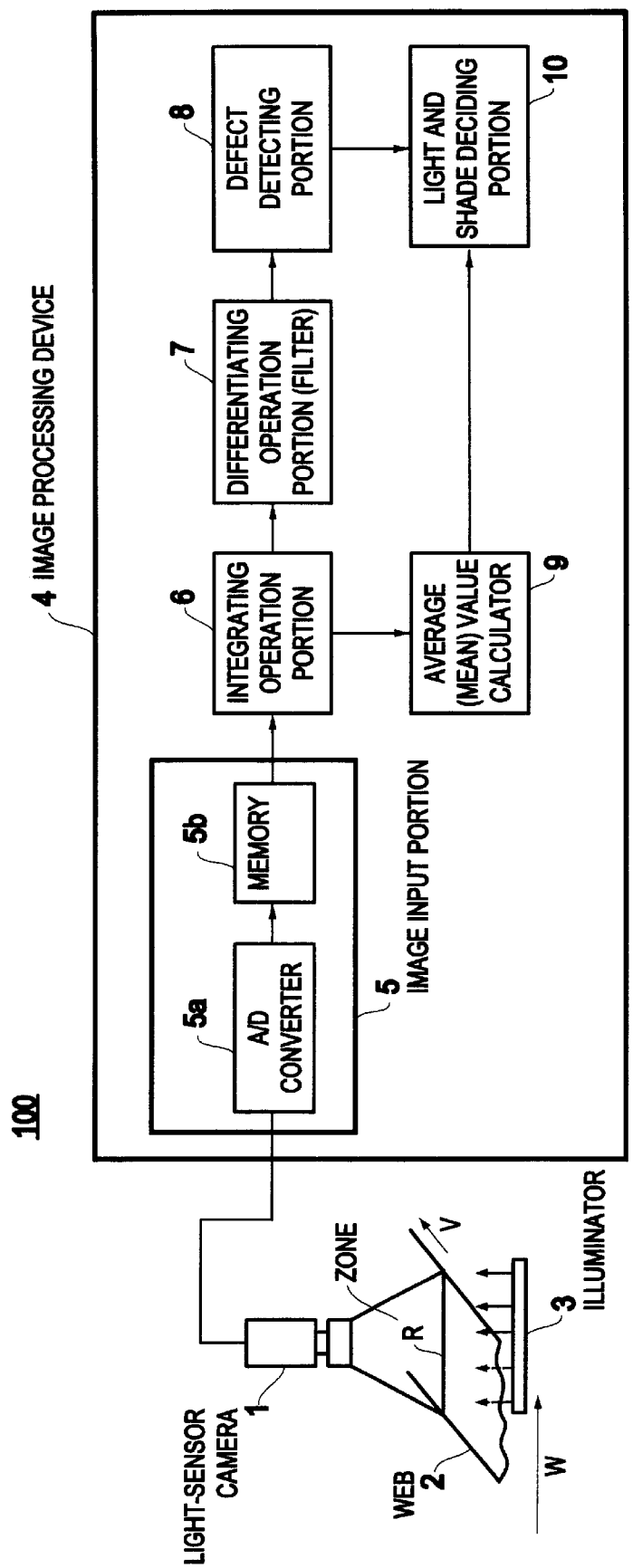
FIG. 1 is a block diagram showing a light-and-shade inspecting apparatus 100 according to a preferred embodiment of the present invention.

FIG. 1 is a functional block diagram showing a light-and-shade inspecting apparatus 100 for use, for example, in a web inspection, as a preferred embodiment of the present invention.

The light-and-shade inspecting apparatus 100 of the present invention includes a line-sensor camera 1 for picking up an image of a web 2 as an object to be inspected having a substantially constant width and traveling in one direction (e.g., a direction transverse to a scanning direction of the pick-up), an illuminator 3 for illuminating a zone R on the web over which the camera 1 picks up the web image, and an image processing device 4 for processing an image data, based on the web image picked up by the camera 1, to inspect light-and-shade defects on the web 2.

The line-sensor camera 1 includes 1024 photoreceptors (e.g., a charge-coupled device (CCD)) arranged in an array along a line and disposed above a central portion in a width direction W or across the width of the web 2 and in a parallel relation to the width direction. The illuminator 3 is placed below the web 2 so as to illuminate or light up the web zone R to be picked up by the camera 1 from a back side of the web 2.

As shown in FIG. 1, the image processing device 4 includes an image input portion 5 coupled to an output of the camera 1, an integrating operation portion 6 coupled to an output of the image input portion 5, a differentiating operation portion (e.g., filter) 7 coupled to an output of the integrating operation portion 6, a defect detecting portion 8 coupled to an output of the differentiating operation portion 7, an average (mean) value calculating portion 9 coupled to an output of the integrating operation portion 6, and a light-and-shade deciding portion 10 coupled to outputs of the average value calculating portion 9 and defect detecting portion 8.

The image input portion 5 includes an analog-to-digital (A/D) converter 5a for performing an A/D conversion of an analog signal of the picked-up image outputted from the camera 1, and for producing a digitized image signal, and a memory 5b for storing, as image data, the image signals produced by digitizing analog image signals obtained through a plurality of scans of the camera 1. As a result, the image signals picked up by the camera 1 are captured in the image processing device 4.

Hereinafter, the light-and-shade inspecting apparatus 100 according to the preferred embodiment of the present invention will be described in detail with reference to FIG. 2.

Figure 2:
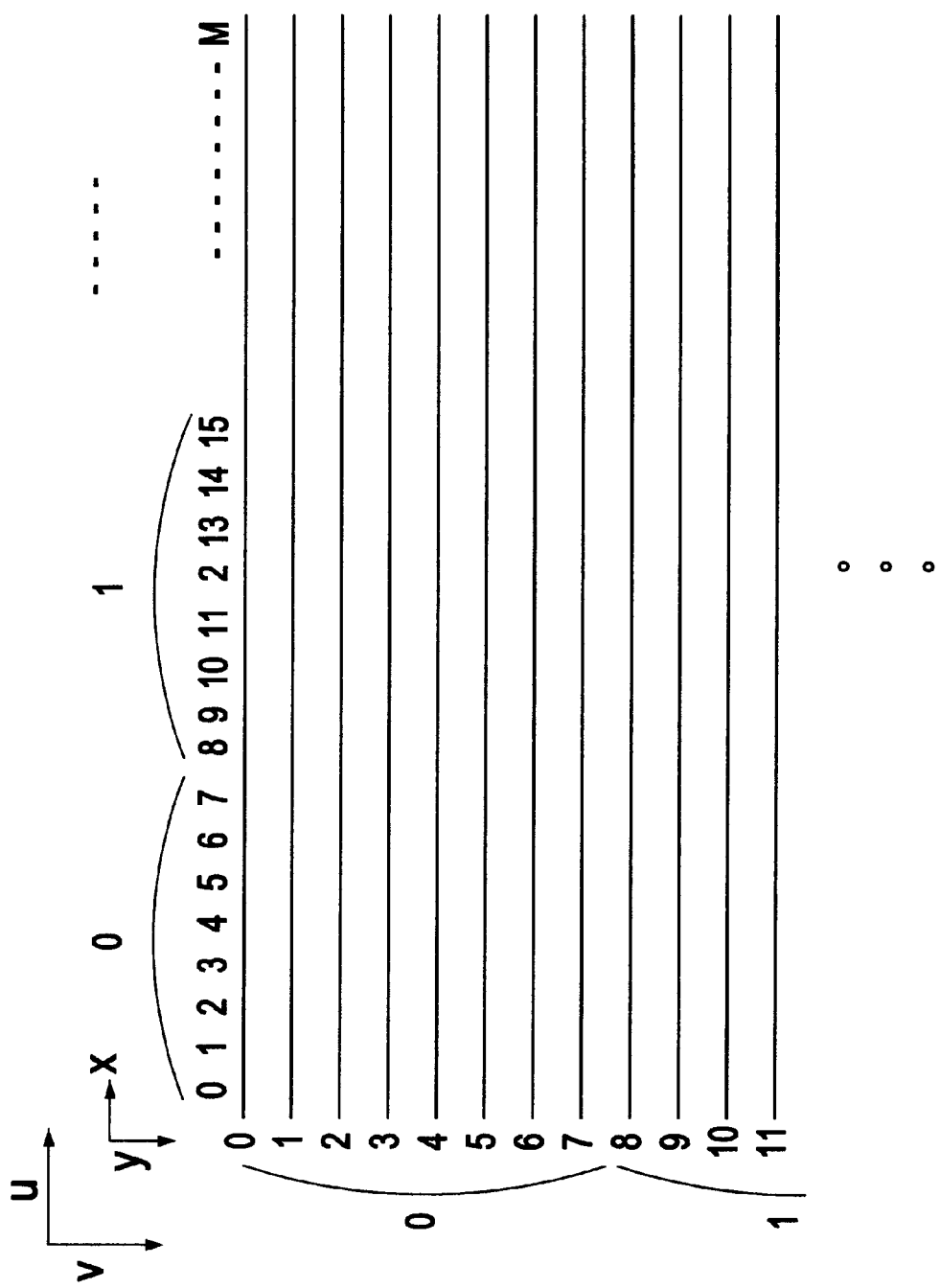
FIG. 2 is a schematic diagram showing a data structure which is stored into a memory 5b of the light-and-shade inspecting apparatus 100 of FIG. 1.

FIG. 2 shows a data structure which is captured into the memory 5b. In FIG. 2, a horizontal axis (e.g., X-axis) illustrates a region of data positions which is scanned through one scan of the line-sensor camera 1, and an X-coordinate thereon indicates a position of the line-sensor which corresponds to a positional coordinate on the web 2 in the width direction. In the preferred embodiment as shown, a positional coordinate of x=0 corresponds to an end or its neighboring portion of the web, whereas a positional coordinate of x=M corresponds to the other end or its neighboring portion of the web. In this embodiment, it is assumed that 1024 photoreceptors are used to pick up an image across the web's width (i.e., M=1024).

In FIG. 2, a vertical axis (e.g., Y-axis) indicates the number of scans of the line-sensor camera 1 at respective positional coordinates (x) and has reference numerals 1 through 11 as the scan number affixed thereon. For example, the scan number 0 indicates a first scan of the line-sensor camera 1.

Figure 3:
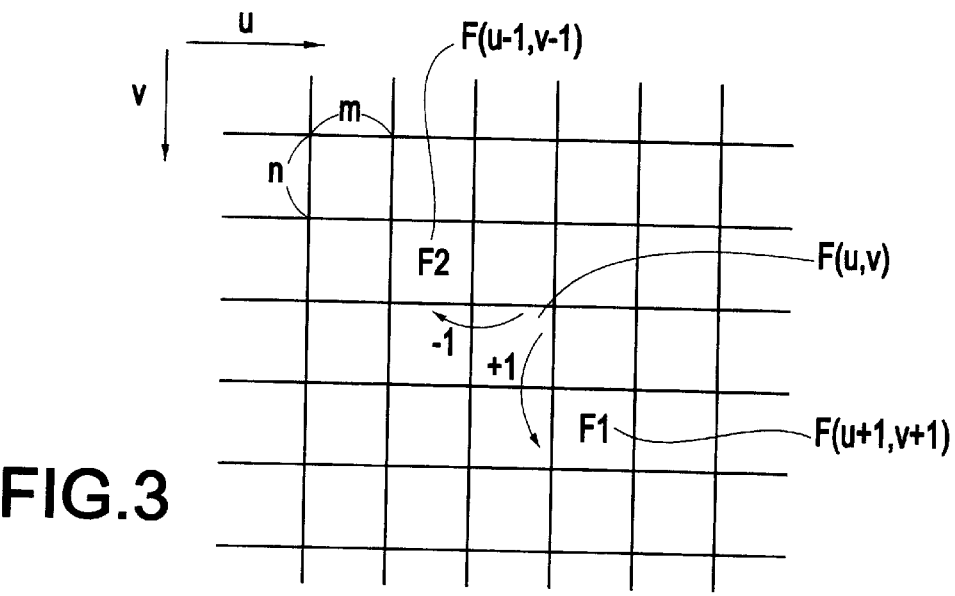
FIG. 3 is a schematic diagram showing a status of image data in a form of divided meshes thereof.
Figure 4:
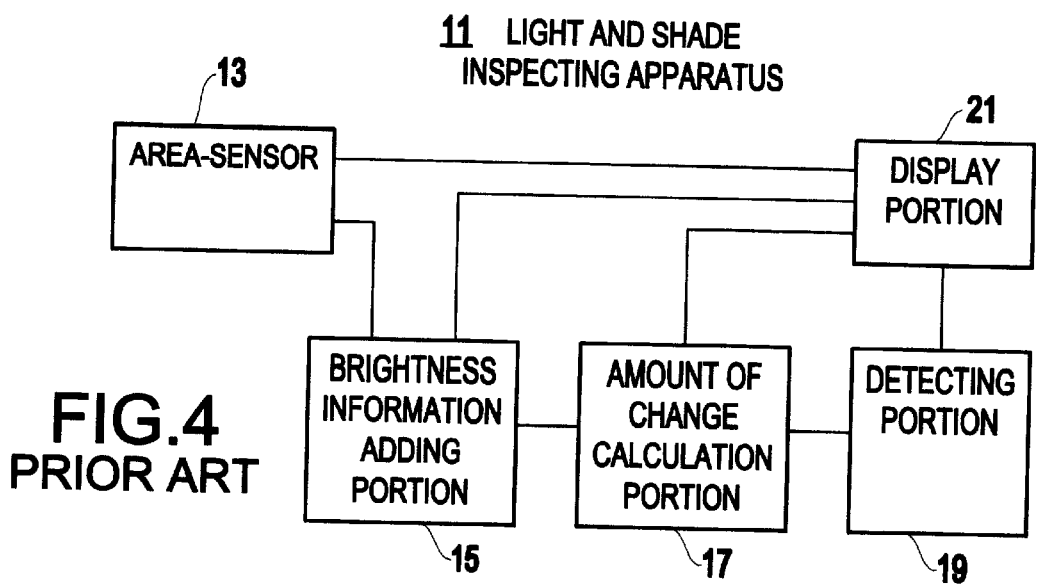
FIG. 4 is a functional block diagram showing a conventional light-and-shade inspecting apparatus 11.
Figure 5:
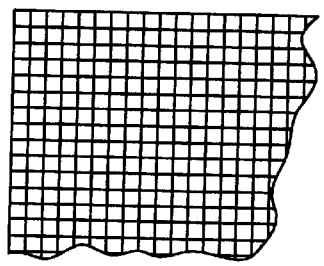
FIG. 5 is a schematic diagram showing an image in a grid form.

In FIG. 2, u numbers are labeled, each u being organized every m positions (e.g., 8 positions) sequentially. Similarly, v numbers are labeled, each v being organized every n scans (e.g., 8 scans) sequentially. Therefore, a u-v coordinate system, as shown in FIG. 3, indicates the respective coordinates of meshes by which the full image data (pixels) is divided into meshes of m×n.

Hence, u and v are respectively expressed by the following equations using Gaussian notation "[ ]".

$$u=[x/m] \quad (1)$$

$$v=[y/n] \quad (2)$$

In this embodiment, it is assumed that each value of m and n is 8, as mentioned above. However, their values may be arbitrarily set, (e.g., selectively adjusted) depending on the sizes of low contrast light-and-shade defects. For example, if a defective area is large, then the respective values of m and n can be increased according to its defective area size.

The integrating operation portion 6, as shown in FIG. 1, sections (e.g., divides) the image data, as shown in FIG. 2, into meshes each of which is of m×n pixels, and then integrates the image data (e.g., brightness or lightness information) within each mesh to obtain an integrated image represented by an integrated value F(u, v). This integration is expressed by the following equation:

$$F(u,v)=\Sigma \ \Sigma f(mu+u',nv+v') \quad (3)$$

wherein, the addition about u' is performed from 0 to m−1 (e.g., corresponding to m positions) and the addition about v' is performed from 0 to n−1 (e.g., corresponding to n scans).

The differentiating operation portion 7 obtains a difference between each pair of two values of integrated images F(u, v) which are present in different meshes apart from each other by a predetermined interval, to provide a differentiated image D(u, v), as follows:

$$D(u,v)=|F(u+\Delta u,v+\Delta v)-F(u-\Delta u,v-\Delta u)| \quad (4)$$

wherein, each of Δu and Δv in the above equation represents an interval between two meshes used for obtaining the difference and 1 is used for both of them in this embodiment. Therefore, if F1 is F(u+Δu, v+Δv) (i.e., F(u+1, v+1), then F2 to be subtracted by F1 will be F(u−Δu, v−Δv) (i.e., F(u−1, v−1)).

The defect detecting portion 8 judges whether a defect (or defects) exists in either of meshes whose functions Fs are subjected to the differentiating processing, on condition that a value of D(u, v) obtained from equation (4) is larger than a predetermined value T1 as follows (e.g., it will be judged whether there exists a defect in any one of F1 or F2.):

$$D(u,v)>T1 \quad (5)$$

The average value calculating portion 9 calculates an average A(u) of the integrated image F(u, v) as follows:

$$A(u)=(\Sigma F(u,v'))/N \quad (6)$$

wherein, the addition in equation (6) is performed in v' from N·i to N·i+N−1. Here, i is expressed by i=[y/N] using Gaussian notation "[ ]", and N is any average length.

The light-and-shade deciding (e.g., judging) portion 10 uses the two integrated images F(u+Δu, v+Δv) and F(u−Δu, v−Δv) from which the respective differentiated values D(u, v) are obtained as the equation (4) and the two average values A(u+Δu) and A(u−Δu) obtained through equation (6) to subtract the average, values in the respective coordinates from the integrated images, respectively, as follows:

$$D+=F(u+\Delta u,v+\Delta v)-A(u+\Delta u) \quad (7)$$

$$D-=F(u-\Delta u, v-\Delta v)-A(u-\Delta u) \quad (8)$$

Then, the deciding (judging) portion 10 judges light and shade by using the above resultant subtracted values as the following (a) and (b):

(a) If the absolute value of D+ is larger than that of D− (|D+|≧|D−|), then F(u+Δu, v+Δv) is decided to be a defect, and in the case of D+≧0, the detect is further decided to be a light defect, or in the case of D+<0, the defect is further decided to be a shade defect.

(b) If the absolute value of D+ is not larger than that of D− (|D+|<|D−|), then F(u−Δu, v−Δv) is decided to be a defect, and in the case of D−≧0, the detect is further decided to be a light defect, or in the case of D−<0, the defect is further decided to be a shade defect.

The foregoing description of the preferred embodiment of the invention has been presented for purposes of illustration and description. It is not intended to be exclusive or to limit the invention to the precise form disclosed, and modifications and variations are possible in light of the above teachings or may be acquired from practice of the invention.

For example, the line-sensor of this embodiment includes 1024 photoreceptors, but the present invention is not limited to this number of photoreceptors. Also, an area-sensor may be employed instead of the line-sensor, but the principle of the present invention remains the same.

As described above, the method of the present invention obtains an image data of an object to be inspected by picking up an image of the object, divides the obtained image data into a mesh pattern of meshes which are equivalent in area to each other, obtains an integrated image by adding together the image data within each divided mesh, obtains a differentiated image by performing a difference operation between each pair of integrated images which are present in predetermined pairs of meshes apart from each other, compares a value obtained from the differentiated image with a predetermined value to detect a portion, as a defect, which is partially different in lightness from the other on the object, calculates an average of the integrated image, and, based on this average value and two values of two integrated images which constitute a defect and which have been subjected to the difference operation, judges whether the defect is a light defect or a shade defect.

Therefore, unlike the conventional apparatus and techniques, low contrast defects can be detected reliably by distinguishing light and shade from each other and without mistaking a single defect as two separate defects.

What is claimed is:

1. A light-and-shade inspecting apparatus for picking up an image of an object to be inspected, and based on an image data thereof inspecting a light and shade on the object, comprising:

an image pick-up device adapted for picking up an image of the object to output an image data;

an integrated image calculating portion adapted for dividing the image data outputted from said image pick-up device into a mesh pattern of meshes which are equivalent in area to each other and then adding together the image data within each of the divided meshes to obtain an integrated image which is represented by F(u,v)= ΣΣf(mu+u',nv+v'), wherein u and v represent a u-v coordinate system of said meshes by which said image data is divided into said meshes of m×n pixels;

a differentiated image calculating portion adapted for performing a difference operation between each pair of meshes separated by a predetermined interval from each other with respect to their corresponding two integrated images obtained by said integrated image calculating portion, wherein said difference operation is represented by D(u,v)=|F(u+Δu, v+Δv)−F(u−Δu, v−Δv)| and wherein each of Δu and Δv represents said predetermined interval between two meshes used for obtaining the difference value;

a defect detecting portion adapted for comparing a value obtained by said differentiated image calculating portion with a predetermined value to detect a defect portion which is partially different in luminance from other portions on the object;

an average value calculating portion adapted for calculating an average value of the integrated image obtained by said integrated image calculating portion; and a light-and-shade deciding portion adapted for deciding whether the defect detected by said defect detecting portion comprises a light defect or a shade defect based on the average value obtained by said average value calculating portion ad values of the integrated images in respective pairs of meshes separated by the predetermined interval from each other which have been subjected to the difference operation.

2. The light-and-shade inspecting apparatus as claimed in claim 1, wherein said light-and-shade deciding portion subtracts the average values of the integrated images in the respective pairs of meshes separated from each other from the respective values of the integrated images to produce the respective subtracted values, and wherein, when one of the subtracted values is larger in absolute value than another of the subtracted values and the subtracted value in connection with the mesh corresponding to the one of the subtracted values is larger than zero, said light-and-shade deciding portion decides the defect in the mesh corresponding to the one of the subtracted values to comprise a light defect.

3. The light and shade inspecting apparatus as claimed in claim 1, wherein said light-and-shade deciding portion subtracts the average values of the integrated images in the respective pairs of meshes apart from each other from the respective values of the integrated images to produce the respective subtracted values, and, wherein, when one of the subtracted values is larger in absolute value than another of the subtracted values and the subtracted value in connection with the mesh corresponding to the one of the subtracted values is negative, said light-and-shade deciding portion decides the defect in the mesh corresponding to the one of the subtracted values to comprise a shade defect.

4. The light and shade inspecting apparatus as claimed in claim 2, wherein said light-and-shade deciding portion subtracts the average values of the integrated images in the respective pairs of meshes apart from each other from the respective values of the integrated images to produce the respective subtracted values, and, wherein, when one of the subtracted values is larger in absolute value than another of the subtracted values and the subtracted value in connection with the mesh corresponding to the one of the subtracted values is negative, said light-and-shade deciding portion decides the defect in the mesh corresponding to the one of the subtracted values to comprise a shade defect.

5. The light and shade inspecting apparatus as claimed in claim 1, wherein said light-and-shade deciding portion subtracts the average values of the integrated images in the respective pairs of meshes apart from each other from the respective values of the integrated images to produce the respective subtracted values.

6. A light-and-shade inspecting apparatus for inspecting an object, comprising:

an integrated image calculator for dividing an image data, input thereto and related to the object, into a mesh pattern of meshes and then adding together the image data within each of the divided meshes to obtain an integrated image which is represented by $F(u,v)=\Sigma\Sigma f(mu+u',nv+v')$, wherein u and v represent a u-v coordinate system of said meshes by which said image data is divided into said meshes of m×n pixels;

a differentiated image calculator for performing a difference operation between each pair of meshes separated by a predetermined interval from each other with respect to their corresponding two integrated images obtained by said integrated image calculator, wherein said difference operation is represented by $D(u,v)=|F(u+\Delta u, v+\Delta v)-F(u-\Delta u, v-\Delta v)|$ and wherein each of $\Delta u$ and $\Delta v$ represents said predetermined interval between two meshes used for obtaining the difference value;

a defect detector for comparing a value obtained by said differentiated image calculator with a predetermined value to detect a defect portion which is at least partially different in luminance from other portions on the object;

an average value calculator for calculating an average value of the integrated image obtained by said integrated image calculator; and a light-and-shade judging unit for judging whether the defect detected by said defect detector comprises a light defect based on the average value obtained by said average value calculating portion and values of the integrated images in respective pairs of meshes separated by the predetermined interval from each other which have been subjected to the difference operation.

7. The light-and-shade inspecting apparatus as claimed in claim 6, wherein said light-and-shade judging unit subtracts the average values of the integrated images in the respective pairs of meshes separated from each other from the respective values of the integrated images to produce the respective subtracted values.

8. The light-and-shade inspecting apparatus as claimed in claim 7, wherein, when one of the subtracted values is larger in absolute value than another of the subtracted values and the subtracted value in connection with the mesh corresponding to the one of the subtracted values is larger than zero, said light-and-shade judging unit judges the defect in the mesh corresponding to the one of the subtracted values to comprise a light defect.

9. The light-and-shade inspecting apparatus as claimed in claim 7, wherein, when one of the subtracted values is larger in absolute value than another of the subtracted values and the subtracted value in connection with the mesh corresponding to the one of the subtracted values is negative, said light-and-shade judging unit judges the defect in the mesh corresponding to the one of the subtracted values to comprise a shade defect.

10. The light-and-shade inspecting apparatus as claimed in claim 6, wherein said meshes are substantially equivalent in area to one another.

11. The light-and-shade inspecting apparatus as claimed in claim 6, further comprising:

an image pick-up device for picking up an image of the object to output the image data to said integrated image calculator.

12. An image processing apparatus for a light-and-shade inspecting system for inspecting an object, comprising:

means for dividing an image data, input thereto and related to the object, into a mesh pattern of meshes and then adding together the image data within each of the divided meshes to obtain an integrated image which is represented by $F(u,v)=\Sigma\Sigma f(mu+u',nv+v')$, wherein u and v represent a u-v coordinate system of said meshes by which said image data is divided into said meshes of m×n pixels;

means for performing a differential operation between each pair of meshes apart by a predetermined interval from each other with respect to their corresponding two integrated images obtained by said dividing means, wherein said differential operation is represented by $D(u,v)=|F(u+\Delta u, v+\Delta v)-F(u-\Delta u, v-\Delta v)|$ and wherein each of $\Delta u$ and $\Delta v$ represents said predetermined interval between two meshes used for obtaining the difference value;

means for comparing a value obtained by said differential operation performing means with a predetermined value to detect a defect portion which is at least partially different in luminance from other portions on the object;

means for calculating an average value of the integrated image obtained by said dividing means; and means for judging whether the defect detected by said comparing means comprises a light defect based on the average value obtained by said average value calculating means and values of the integrated images in respective pairs of meshes separated by the predetermined interval from each other which have been subjected to the difference operation.

13. The image processing apparatus as claimed in claim 12, wherein said judging means subtracts the average values of the integrated images in the respective pairs of meshes separated from each other from the respective values of the integrated images to produce the respective subtracted values.

14. The image processing apparatus as claimed in claim 13, wherein, when one of the subtracted values is larger in absolute value than another of the subtracted values and the subtracted value in connection with the mesh corresponding to the one of the subtracted values is larger than zero, said judging means judges the defect in the mesh corresponding to the one of the subtracted values to comprise a light defect.

15. The image processing apparatus as claimed in claim 13, wherein, when one of the subtracted values is larger in absolute value than another of the subtracted values and the subtracted value in connection with the mesh corresponding to the one of the subtracted values is negative, said judging means judges the defect in the mesh corresponding to the one of the subtracted values to comprise a shade defect.

16. The image processing apparatus as claimed in claim 12, wherein said meshes are substantially equivalent in area to one another.

17. A light and shade inspecting method for picking up an image of an object to be inspected, and based on an image data thereof inspecting a light and shade on the object, comprising:

picking up an image of the object to obtain an image data;

dividing an image comprising the image data into a mesh pattern of meshes which are equivalent in area to each other, and then adding together the image data within each of the divided meshes to obtain an integrated image which is represented by $F(u,v)=\Sigma\Sigma f(mu+u',nv+v')$, wherein u and v represent a u-v coordinate system of said meshes by which said image data is divided into said meshes of m×n pixels;

performing a difference operation between each pair of meshes separated by a predetermined interval from each other with respect to their corresponding two integrated images to obtain a differentiated image, wherein said difference operation is represented by $D(u,v)=|F(u+\Delta u, v+\Delta v)-F(u-\Delta u, v-\Delta V)|$ and wherein each of $\Delta u$ and $\Delta v$ represents said predetermined interval between two meshes used for obtaining the differentiated image;

comparing a value obtained from the differentiated image with a predetermined value to detect as a defect a portion which is partially different in lightness from the other on the object;

calculating an average value of the integrated image; and deciding whether the defect comprises a light defect or a shade defect based on the average value and values of the integrated images in the respective pairs of meshes apart by the predetermined interval from each other which have been subjected to the difference operation.

18. A method of inspecting an object, comprising:

dividing an image comprising image data of the object into a mesh pattern of meshes, and then adding together the image data within each of the divided meshes to obtain in integrated image which is represented by $F(u,v)=\Sigma\Sigma f(mu+u',nv+v')$, wherein u and v represent a u-v coordinate system of said meshes by which said image data is divided into said meshes of m×n pixels;

performing a difference operation between each pair of meshes separated by a predetermined interval from each other with respect to their corresponding two integrated images to obtain a differentiated image, wherein said difference operation is represented by $D(u,v)=|F(u+\Delta u, v+\Delta v)-F(u-\Delta u, v-\Delta v)|$ and wherein each of $\Delta u$ and $\Delta v$ represents said predetermined interval between two meshes used for obtaining the differentiated image;

comparing a value obtained from the differentiated image with a predetermined value to detect as a defect a portion which is at least partially different in lightness from other portions on the object;

calculating an average value of the integrated image; and judging whether the defect comprises a light defect or a shade defect based on the average value and values of the integrated images in the respective pairs of meshes apart by the predetermined interval from each other which have been subjected to the difference operation.

19. The method as claimed in claim 18, wherein said judging steps comprises subtracting the average values of the integrated images in the respective pairs of meshes separated from each other from the respective values of the integrated images to produce the respective subtracted values.

20. The method as claimed in claim 19, wherein, when one of the subtracted values is larger in absolute value than another of the subtracted values and the subtracted value in connection with the mesh corresponding to the one of the subtracted values is larger than zero, said judging step judges the defect in the mesh corresponding to the one of the subtracted values to comprise a light defect.

21. The method as claimed in claim 19, wherein, when one of the subtracted values is larger in absolute value than another of the subtracted values and the subtracted value in connection with the mesh corresponding to the one of the subtracted values is negative, said judging step judges the defect in the mesh corresponding to the one of the subtracted values to comprise a shade defect.

22. The method as claimed in claim 18, wherein said meshes are substantially equivalent in area to one another.

23. The method as claimed in claim 18, further comprising:

picking up, with an image pick-up device, an image of the object to produce the image data to be divided into the mesh pattern.

* * * * *